United States Patent [19]

Winston et al.

[11] Patent Number: 5,614,175
[45] Date of Patent: Mar. 25, 1997

[54] STABLE SINGLE-PART COMPOSITIONS AND THE USE THEREOF FOR REMINERALIZATION OF LESIONS IN TEETH

[75] Inventors: A. E. Winston, East Brunswick; Norman Usen, Marlboro, both of N.J.

[73] Assignee: Enamelon Inc., East Brunswick, N.J.

[21] Appl. No.: 691,328

[22] Filed: Aug. 2, 1996

Related U.S. Application Data

[62] Division of Ser. No. 512,287, Aug. 8, 1995, Pat. No. 5,571,502.

[51] Int. Cl.$^6$ ................ A61K 7/16; A61K 7/18
[52] U.S. Cl. ................ 424/52; 424/49; 424/57; 424/401; 424/463; 424/489; 424/490
[58] Field of Search ................ 424/49, 52, 57, 424/401, 463, 489, 490

[56] References Cited

U.S. PATENT DOCUMENTS

| | | | |
|---|---|---|---|
| 2,605,229 | 7/1952 | Marcus | 252/317 |
| 3,679,360 | 7/1972 | Rubin | 23/109 |
| 3,913,229 | 10/1975 | Driskell et al. | 32/15 |
| 4,048,300 | 9/1977 | Tomlinson et al. | 424/52 |
| 4,080,440 | 3/1978 | DiGiulio et al. | 424/49 |
| 4,083,955 | 4/1978 | Grabenstetter et al. | 424/49 |
| 4,097,935 | 7/1978 | Jarcho | 3/1.9 |
| 4,108,980 | 8/1978 | Duff | 424/52 |
| 4,177,258 | 12/1979 | Gaffar et al. | 424/52 |
| 4,183,915 | 1/1980 | Gaffar et al. | 424/52 |
| 4,233,288 | 11/1980 | Cornell | 424/48 |
| 4,348,381 | 9/1982 | Gaffar et al. | 424/49 |
| 4,397,837 | 8/1983 | Raaf et al. | 424/51 |
| 4,405,600 | 9/1983 | Besic | 424/57 |
| 4,436,720 | 3/1984 | Pakhomov et al. | 424/52 |
| 4,515,770 | 5/1985 | Besic | 424/49 |
| 4,518,430 | 5/1985 | Brown et al. | 106/35 |
| 4,556,561 | 12/1985 | Brown et al. | 424/151 |
| 4,606,912 | 8/1986 | Rudy et al. | 424/52 |
| 4,610,873 | 9/1986 | Rudy et al. | 424/52 |
| 4,612,053 | 9/1986 | Brown et al. | 706/35 |
| 4,672,032 | 6/1987 | Slavkin et al. | 435/68 |
| 4,808,401 | 2/1989 | Gaffar et al. | 424/49 |
| 4,925,655 | 5/1990 | Smigel et al. | 424/52 |
| 5,037,639 | 8/1991 | Tung | 424/57 |
| 5,268,167 | 12/1993 | Tung | 424/52 |
| 5,427,768 | 6/1995 | Tung | 424/52 |
| 5,437,857 | 8/1995 | Tung | 424/52 |
| 5,460,803 | 10/1995 | Tung | 424/57 |

FOREIGN PATENT DOCUMENTS 9418938  9/1994  WIPO.

*Primary Examiner*—Hoa Van Le
*Attorney, Agent, or Firm*—Depaoli & Frenkel, P.C.

[57] ABSTRACT

This invention relates to non-aqueous compositions and methods utilizing same which are useful to remineralize subsurface dental enamel. More specifically, this invention relates to stable, single-part compositions containing calcium and phosphate salts which may be in a hydrophilic, non-aqueous vehicle and which when applied to lesions in dental enamel result in remineralization of subsurface dental enamel and/or mineralization of tubules in dentin thereby counteracting caries and/or hypersensitivity.

26 Claims, No Drawings

STABLE SINGLE-PART COMPOSITIONS AND THE USE THEREOF FOR REMINERALIZATION OF LESIONS IN TEETH

This application is a division of application Ser. No. 08/512,287, filed Aug. 8, 1995, U.S. Pat. No. 5,571,502.

BACKGROUND OF THE INVENTION

1. Field of the Invention

This invention relates to non-aqueous compositions and processes utilizing same which are useful to remineralize subsurface dental enamel. More specifically, this invention relates to stable, single-part compositions containing calcium and phosphate salts which may be in a hydrophilic, non-aqueous vehicle and which when applied to lesions in dental enamel result in remineralization of subsurface dental enamel and/or mineralization of tubules in dentin thereby counteracting caries and/or hypersensitivity

2. The Prior Art

The primary component of the enamel and dentin in teeth is calcium phosphate in the form of calcium hydroxyapatite. This material is highly insoluble at normal oral pHs. However, carious lesions form In teeth, when they are subjected to acids produced from the glycolysis of sugars by the action of various oral bacteria. This is because calcium phosphate salts are more soluble in acidic media.

Saliva is supersaturated with respect to calcium and phosphate ions. Saliva therefore helps protect teeth against demineralization and can slowly remineralize teeth which have become demineralized by acids. It is well known that the presence of fluoride ions can enhance the natural remineralization process and this is one of the accepted mechanisms by which fluoride toothpastes and rinses protect against caries. The efficacy of fluoride containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of sally a the addition of higher levels of dissolved calcium and phosphate ions is not easily accomplished.

Remineralization of dental enamel has been carried out experimentally both in vivo and in vitro. Some studies have concentrated on the remineralizing properties of saliva and synthetic solutions supersaturated with respect of hydroxyapatite. Such studies comprise the subject matter of U.S. Pat. Nos. 3,679,360 (Rubin) and 4,097,935 (Jarcho).

Generally, the supersaturated solutions or slurries used in these patents for remineralization experiments have been prepared from a single form of calcium phosphate. When a carious lesion is flooded with one of these supersaturated solutions, the calcium and phosphate ions in the form of precipitated hydroxyapatite remineralize the lesion.

However, these solutions are impractical for use for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because they cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solution, the pH of the solution changes. Unless the old solution is removed from contact with the tooth material, the solution may become too acidic or alkaline and damage the dental tissue.

U.S. Pat. No. 4,080,440 (Digiulio et al) discloses a metastable solution of calcium and phosphate ions at a low pH (between 2.5 to 4.0) underwhich conditions the solubility of calcium phosphate salts is high. After penetration of the solution into demineralized enamel, remineralization results from the precipitation of calcium phosphate salts when the pH rises. Fluoride ions can be included in the metastable solution. A significant disadvantage of the use of metastable solutions is that the relatively low pH might demineralize the dental enamel and/or injure other tissue.

U.S. Pat. Nos. 4,177,258, 4,183,915 and 4,348,381 (Gaffar et el) provide for a remineralizing solution containing supersaturated concentrations of calcium ions, phosphate ions and a fluoride source stabilized by the presence of an antinucleating agent such as diamine tetramethylenephosphonic acid, ethylenediamine tetramethylenephosphonic acid and 2-phosphonobutane-tricarboxylic acid-1,2,4, or the water-soluble salts thereof. This solution is preferably adjusted to the neutral pH range where it is alleged to most effectively remineralize sub-surface lesions. Even though the antinucleating agent would be expected to stabilize the solution, equilibrium of the supersaturated concentrations is still found difficult to maintain and avoid precipitation of hydroxyapatite and changes in the pH of the solution.

U.S. Pat. No. 4,083,955 (Grabenstetter et al) and U.S. Pat. No. 4,397,837 (Raaf et al) provide a process for remineralizing demineralized enamel by the consecutive treatment of tooth surfaces with separate solutions containing calcium ions and phosphate ions. In this process fluoride ions may be present in the phosphate solutions. It is immaterial which ionic solution is used to treat the teeth first. By sequentially applying calcium and phosphate ions to the tooth surface high concentrations of the ions are able to penetrate into lesions in solution form, where they precipitate as a calcium phosphate salt when ions from the second treatment solution diffuse in. While apparently successful this method involves the inconvenience of a plurality of sequential applications which can also be found to be time consuming.

Thus, the problem with known remineralization compositions and techniques is that there is not a one-part, stable remineralizing composition that may be suitably prepared as a mouthwash or rinse and can be incorporated into other dentifrice compositions such as a toothpaste or gel, troche, chewing gum, lozenge and the like.

There is a need for a method of remineralizing dental enamel which employs a stable, single-part remineralizing composition and does not require excessive amounts of solution and inordinately long or frequent exposure times.

It is the object of the present invention to provide a single-part stable composition and process for the remineralization and the prevention of demineralization of human teeth, which process and composition are capable of effectively incorporating calcium ions, phosphate ions and fluoride ions into the dental enamel, the composition also being easily usable by the consumer and not differing significantly, in flavor and appearance, from customary dental cosmetics.

SUMMARY OF THE INVENTION

In accordance with the present invention the problems of remineralization, without demineralization are solved by applying to the teeth a stable, single-part composition which contains remineralization components which do not react with one another until introduced into the oral cavity. The composition contains at least one water-soluble calcium compound and at least one water-soluble inorganic phosphate compound and, optionally, at least one water-soluble fluorine compound. In this way the ions which effect remineralization can be absorbed by the dental enamel and their subsequent reaction causes rehardening of demineralized areas in the dental enamel.

It has been found that effective remineralizing treatments can be prepared by providing non-aqueous solutions or preparations of soluble salts containing high concentrations of calcium, phosphate and, if desired, fluoride ions and applying them to teeth at moderate pHs. However, the calcium ions must be prevented from reacting with the phosphate ions or fluoride ions until immediately before use.

In one embodiment of the invention, a non-aqueous toothpaste or gel is provided comprising at least one water-soluble calcium salt, at least one water-soluble phosphate salt, if desired at least one water-soluble fluoride compound yielding fluoride ions, and a hydrophilic, non-aqueous vehicle which is water soluble and wherein, when the composition is contacted with water, the resulting solution has a pH of between about 4.5 and 10.0.

The stable, single-part system, in the form of toothpastes, gels, professional gels, i.e., those which are applied professionally or are obtained by a prescription, mouthwashes or rinses, troches, chewing gums, lozenges, and the like contain from about 0.05% to about 15% water-soluble calcium salt, from about 0.05% to 15% water-soluble phosphate salt, if desired from about 0.01% to 5.0% fluoride-releasing agent, and suitable pH adjusting compounds, i.e., acids or bases, such that the pH is between about 4.5 and 10.0, and preferably between about 5.0 and 7.0. Compositions may be applied directly to the teeth and solubilized with saliva or are mixed with water, solubilized and immediately applied to the teeth being treated. It has been found that such combinations produce rapid remineralization of lesions and are much more effective than conventional fluoride containing toothpastes in remineralizing teeth.

The stable, single-part system may also be in the form of a dry-mix concentrated product which may be diluted with water to prepare a mouthwash or otherwise treated or mixed to make other products. The dry-mix product may be in the form of a powder, granular material, flake, tablet or the like. This embodiment contains from about 1.0% to 80.0% of the calcium salt and the phosphate salt. Other adjuvants may, of course, be included.

The compositions of the invention give substantially improved remineralization and prevention of demineralization of human teeth as compared with prior art compositions.

The disadvantages of the prior art methods are overcome by the present invention which effects subsurface remineralization rather than surface remineralization. Since dental caries begins as a subsurface demineralization of the dental enamel, subsurface remineralization arrests and repairs the carious lesion before any permanent structural damage to the tooth occurs. The present invention does not require preparation of the enamel surface, capping of the tooth, or removal of decay products. Further, the present invention may be conveniently practiced by the public without substantially changing their dental care habits.

DESCRIPTION OF THE INVENTION

The present invention lies in the discovery that dental enamel may be remineralized by the application of certain soluble salts yielding ions which will react to form a desirable remineralizing precipitate. The crux of the invention consists of the use of stable, one-part system in the form of paste, gel, granules, powder, flakes, non-aqueous solution, etc, containing water-soluble salts which are placed in contact with the tooth surface. Saliva in the mouth causes dissolution of the soluble salts allowing the selected cations and anions to diffuse through the tooth surface to the demineralized subsurface with the cations and anions forming a precipitate which is bound to the tooth structure. As a result, the tooth's subsurface is remineralized when an effective amount of the remineralization system is utilized.

As discussed above, the compositions of the invention are preferably non-aqueous. By "non-aqueous" is meant that the compositions do not include water in such an amount that it will adversely affect the stability required by the remineralization composition of the invention, i.e., the components of the compositions of the invention do not contain significant quantities of free water. However, they may contain salts with water of hydration. Preferably, the compositions of the invention include either no water or only traces of water.

By "effective amount of remineralizing system or agent" is meant an amount when used in accordance with this invention will bring about the remineralizing of teeth having carious lesions, or the mineralizing of normal teeth to prevent caries from forming and to inhibit hypersensitivity by utilizing a toothpaste, gel, or mouthwash having the various components in the amounts set forth below.

Concentrations of the soluble salt are from about 0.05 to 15% or the limit of solubility of the salt. Excess salt can be present, if desired. Concentrations from about 0.10% to 10% are preferred. The concentrations of the soluble salts containing the desired anions are essentially the same as those for the water-soluble salts containing the desired cations.

Although many precipitates are within the broad scope of this invention, by depositing a precipitate less soluble than the original enamel, the remineralized subsurface can be made to be more resistant to demineralization than was the original enamel. When a fluoride salt is utilized which yields fluoride ions, the remineralized enamel is even more resistant to demineralization than was the original enamel.

The concentration of salt containing fluoride ion to the solution may be from about 0.01% to 5.0%, but from about 0.02% to 2.0% is preferred.

In order to effect remineralization of the dental enamel, an effective amount of the desired cartons and antons must be employed in the oral cavity. The amount of solution in the mouth must contain at least 100 ppm of desired cartons and 100 ppm of desired antons and preferably contains more than 1,000 ppm of desired cartons and 1,000 ppm of desired anions. It is preferred to provide a level of fluoride ions between about 20 ppm to 5,000 ppm in the oral cavity from the dentifrice or professionally applied or prescribed gel.

While the length of time of contact between the dissolved salts and the tooth's surface is not critical, it is necessary for the length of time to be great enough to allow diffusion of the ions through the tooth's surface to the demineralized subsurface. It is submitted that at least ten seconds is required for this diffusion and preferably it should be greater than thirty seconds and even longer if possible.

After dissolving in the saliva the solution should have a pH of from about 4.5 to 10.0 and preferably between about 5.0 and 7.0 before and after the precipitation reaction, and be otherwise compatible in the oral environment. While some precipitation may occur upon solubilization or upon application to the teeth, not all of the ions should combine prematurely in the solution to form a precipitate, but must be able to diffuse through the surface of the tooth to a demineralized subsurface area and be able to form an insoluble salt with their respective counterions.

The compositions utilized and the insoluble precipitates must have acceptable levels of toxicity (i.e., the particular ions, in the amounts used in the remineralization process, must be non-toxic).

In a prefer red embodiment of the present invention, the stable, one-part, non-aqueous remineralizing composition contains about 0.05% to 15%, preferably about 0.10% to 10% of a water-soluble calcium salt yielding calcium ions, from about 0.05% to 15%, preferably about 0.10 % to 10%, of a water-soluble phosphate salt yielding phosphate ions and from about 0.01% to 5.0%, preferably from about 0.02% to 2.0%, of a soluble fluoride salt yielding fluoride ions in a hyrophilic, non-aqueous vehicle which is water-soluble. The pH of the composition in the oral cavity is between about 4.5 and 10.0, preferably between about 5.0 and 7.0.

The resulting precipitate is a calcium phosphate or hydroxyapatite, the natural constituent of tooth enamel, with incorporated fluoride ions. Not only does this process result in remineralized enamel, but the remineralized enamel may be more resistant to subsequent demineralization than was the original enamel.

As the calcium compound it is, in principle, possible to employ, in the preparations of the invention, all water-soluble toxicologically harmless calcium compounds. A compound is considered to be water-soluble when at least 0.25 gram thereof dissolves in 100 ml of $H_2O$ at 20° C.

Suitable water-soluble calcium compounds are, for example, calcium chloride, calcium bromide, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate or mixtures of water-soluble calcium compounds. Calcium nitrate is preferred. In the compositions of the invention for the remineralization of human dental enamel, at least about 100 ppm of calcium ions should be present; the upper limit is about 35,000 ppm of calcium ions.

Suitable water-soluble inorganic phosphates within the scope of the present invention are, for example, alkali salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate. The concentration of the phosphate ions is preferably about 100 ppm to 40,000 ppm; solubility in water is defined as in the case of the calcium compounds.

If desired, water-soluble salts yielding both calcium and phosphate ions, such as monobasic-calcium orthophosphate, may be employed. The compositions of the invention for the remineralization or prevention of remineralization of human teeth preferably also contain water-soluble fluoride compounds, the caries-prophylactic activity of which has for a long time been considered to be established.

Suitable fluoride compounds are the alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites.

Organic fluorides, such as the known amine fluorides are also suitable for use in the compositions of the invention.

Water-soluble alkali metal monofluorophosphates such as sodium monofluorophosphate, lithium monofluorophosphate and potassium monofluorophosphate, preferably, sodium monofluorophosphate may be employed. In addition other water-soluble monofluorophosphate salts may be employed including ammonium monofluorophosphate aluminum monofluorophosphate, and the like.

Suitable hydrophilic, non-aqueous vehicles for use in the present invention include polyalkylene glycols, the humectant polyols such as glycerine, propylene glycol, dipropylene glycol and hexylene glycol. Glycerin, propylene glycol and polyethylene glycol are preferred. As used herein, "propylene glycol" includes 1,2-propylene glycol and 1,3-propylene glycol.

For a mouthwash ethyl alcohol could also be used as a vehicle. Such a product would be added to water immediately before being used.

Non-ionic surfactants could be used as the hydrophilic, non-aqueous vehicle in the toothpaste or gel composition of the invention include materials such as polyoxyethylene sorbitan fatty acid esters. Polyoxyethylene fatty acid esters are also suitable for use as the vehicle in the compositions of the invention. An other suitable class of non-ionic surfactants for use in the vehicle in the present invention are polyoxyethylene fatty ethers.

The hydrophilic, non-aqueous, water-soluble vehicles preferably provide a viscosity for the composition suitable for its use as a toothpaste or gel, e.g., between about 50,000 cps. to 600,000 cps. If the selected vehicle does not itself provide the desired viscosity, viscosity modifiers, and/or other vehicle agents can be included to provide such desired viscosity. The use of higher molecular weight polyethylene glycol such as Carbowax 8000 is one preferred means of increasing the viscosity of a non-aqueous system.

Other suitable thickening agents are water-soluble salts of cellulose ethers, such as sodium carboxym ethyl cellulose, hydroxy methyl cellulose, hydroxypropyl cellulose, and hydroxyethyl cellulose. Natural gums such as gum karaya, gum arabic, carrageenan and gum tragacanth, can also be used. Colloidal magnesium aluminum silicate, silica aerogels, silica xerogels, fumed silica, or other finely divided silica can be used as part of the thickening agent for further improved texture.

Typically, hydrophilic, non-aqueous, water-soluble vehicles employed in the toothpaste or gel compositions of the invention are present in an amount of from about 20% to 80%. Preferably, the vehicles are present in an amount of from about 30% to 70%. The amount of hydrophilic, non-aqueous, water-soluble vehicle employed in liquid formations, e.g., mouthwashes, rinses, sprays, and the like is from about 50% to 95%.

In addition to the remineralizing ingredients of the invention, suitable non-aqueous toothpastes and gels can be made by employing in the toothpaste or gel, from about 0.5% to 50%, preferably from about 5% to 40%, of an abrasive, from about 0.2% to 5% of a sudsing agent, from about 0.1% to 5% of a binding agent, and the balance, hydrophilic, non-aqueous vehicle and minors, such as flavor, sweetner, coloring, etc.

The pH of a of the toothpaste or gel containing the active cationlc ingredients must have a pH of from about 4.5 to about 10.0 and, preferably, between about 5.0 and 7.0 when dissolved in saliva.

Suitable abrasives include silica xerogels. Other conventional toothpaste abrasives can be used in the compositions of this invention, and include beta-phase calcium pyrophosphate, dicalcium phosphate dihydrate, anhydrous calcium phosphate, calcium carbonate, zironium silicate, and thermosetting polymerized resins. Silica aerogels and the insoluble metaphosphates such as insoluble sodium metaphosphate can be used. Mixtures of abrasives can be also be used. Silica xerogel abrasives are preferred.

Suitable sudsing agents are those which are reasonably stable and form suds throughout the period of application. Preferably, non-soap anionic or nonionic organic synthetic detergents are employed. Examples of such agents are water-soluble salts of alkyl sulfate having from 10 to 18 carbon atoms in the alkyl radical, such as sodium lauryl sulfate, water-soluble salts of sulfonated monoglycerides of fatty acids having from 10 to 18 carbon atoms, such as sodium monoglyceride sulfonate, salts of $C_{10}$–$C_{18}$ fatty acid amides of taurine, such as sodium N-methyl taurate, salts of $C_{10}$–$C_{18}$ fatty acid esters of isethionic acid, and substantially saturated aliphatic acyl amides of saturated monoaminocarboxylic acids having 2 to 6 carbon a toms, and in which the acyl radical contains 12 to 16 carbon atoms, such as sodium-N-lauryl sarcoside. Mixtures of two or more sudsing agents can be used.

Toothpaste or gel compositions may also contain flavoring agents such as oil of wintergreen, oil of peppermint, oil of spearmint, oil of sassafras, and oil of clove. Toothpaste or gel compositions may also contain sweetening agents such as saccharin, dextrose, levulose, sodium cyclamate, and aspartame Mixtures of sugar with a sweetner, e.g., sucralose, are contemplated.

It is, of course, also possible to manufacture the dentifrice composition in the form of a transparent or translucent gel. This is accomplished by matching the refractive index of the vehicle with the abrasives or inorganic thickeners, if used.

The non-aqueous remineralizing systems herein can also be provided in the form of a mouthwash or similar product e.g., a mouthrinse product. The mouthwash can be made in accordance with the following. Mouthwashes generally comprise an alcohol, e.g., ethyl alcohol and flavoring materials. The alcohol provides an antibacterial effect, solubilizes the flavoring materials and provides a pleasant mouth feeling. Alcohol-free mouthwashes are now, however, gaining in popularity.

An alcohol-free mouth wash would best be provided in the form of a dry powder or tablets which are added to water immediately before use. Such a product would contain 10 to 95% remineralizing salts and the balance would be flavors, sweeteners, and optionally antibacterial, effervesing agents etc.

Examples of suitable flavoring agents include heliotropyl nitrile, wintergreen oil (methyl salicylate), oil of peppermint, oil of assia, oil of anise, oil of cinnamon, and mixtures thereof. Suitable sweetening agents include saccharin, glycerine, sorbitol, levulose, and 6-(tribluoromethyl)-tryptophane and aspartyl phenylalanine methyl ester.

It has been found that with the non-aqueous systems used in the present invention some reaction between the calcium and phosphate ions may, in fact, take place and cause some formation of insoluble calcium phosphate, etc. during storage. The present invention optionally overcomes this problem by including suitable stabilizers which prevent reaction of the calcium ions with the phosphate ions and also with the fluoride ions if they are present.

Any orally acceptable material that stabilizes one or more of the calcium, phosphate and/or fluoride salts during storage of the non-aqueous composition in a closed container can be employed in the present composition. Examples of suitable stabilizing agents include dessicating agents, coating or encapsulating materials and mixtures of such stabilizing agents.

Examples of suitable dessicating agents include magnesium sulfate, sodium sulfate, calcium sulfate, calcium chloride and colloidal silica, e.g., colloidal silica particles sintered together in chainlike formations having surface areas of from about 50 to about 400 square meters per gram such as materials sold under the trademark Cab-O-Sil by Cabot Corp. It is believed that such materials act in stabilizing the compositions of the invention by, for example, absorbing any existing water either present in or contacted with the composition so as to prevent reaction of the calcium, phosphate and/or fluoride salts.

The stabilizing material is included in the composition of the invention in an amount effective so as to inhibit reaction between the calcium, phosphate and/or fluoride salts in the composition during storage in a closed container, but so as to allow release of sufficient calcium phosphate and/or fluoride ions when the composition is contacted with saliva, e.g., during brushing of teeth. Typically, the stabilizing material is included in the compositions of the present invention in an amount of up to about 7.5%, preferably from about 0.1% to 5.0%.

In an embodiment of this invention there is provided a stable single-part non-aqueous dentifrice product for remineralizing dental enamel comprising: (i) from about 0.05% to 15.0%, preferably about 0.10% to 10.0%, water-soluble calcium salt; (ii) from about 0.05% to 15.0%, preferably about 0.10% to 10.0% water-soluble phosphate salt, optionally together with from about 0.01% to 10.0% and preferably from about 0.02% to 5.0% water-soluble fluoride salt, (iii) from about 0 to 7.5% of an orally acceptable dessicating agent; and (iv) wherein when the salts are contacted with water or saliva the pH is between about 4.5 and 10.0 and preferably between about 5.0 and 7.0.

Another method for inhibiting premature reaction of the calcium, phosphate and/or fluoride salts in the dentifrice compositions of the present invention is to provide a coating on or encapsulation thereof, e.g., with an oleophilic or, preferably, a polymeric material, which prevents reaction between the active materials. The presence of the coating on the various salts in the compositions of the present invention prevents reactions of the active material by other substances, for example, by traces of water in or absorbed into the system. Preferably, the coating is an edible coating. Suitable encapsulating or coating materials include oleophilic and other materials such as conventional edible gums, polymers which exhibit proportion ranging from hydrophilic to hydrophobic (water-insoluble), resins, waxes and mineral oils. The coating is preferably rinsable from the mouth.

In accordance with the invention a polymer employed for coating the water-soluble calcium and/or phosphate salt particles and the like of the invention is selected from hydrophilic organic polymers and hydrophobic (water-insoluble) organic polymers and mixtures thereof.

A hydrophilic polymer employed for coating the remineralizing salt particles is selected from water-soluble and water-dispersible organic polymers. A mixture of polymers can be employed, and a content of between about 5.0% to 95.0% of a water-insoluble polymer, based on the coating weight, can be included with a hydrophilic polymer.

The term "hydrophilic" as employed herein refers to an organic polymer which has a water-solubility of at least about one gram per 100 grams of water at 25° C. The term "hydrophobic" or "water-insoluble" as employed herein refers to an organic polymer which has a water solubility of less than about one gram per 100 grams of water at 25° C.

Suitable hydrophilic polymers for coating remineralizing salt particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, and the like.

Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating remineralizing salt particles include polyvinyl acetate, polyacrylamide, polyvinyl chloride, polystyrene, polyethylene, polyurethane, and the like.

The application of the polymer coating to the blend of calcium, phosphate, and other salt particles of the invention process is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethyl formamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the discrete crystallite particles.

The coating thickness on the surface of the salt typically will vary in the range between about 0.1–20 microns. The coating can consist of a single layer or multiple layers. The polymeric coating can constitute between about 5.0% to 50.0% of the total dry weight of the coated particles.

For purposes of release of the core matrix remineralizing calcium phosphate and, if desired, fluoride salts in the encapsulated particles when introduced into the aqueous environment, a surface coating of water-insoluble polymer of the oral cavity may have a content between about 5.0% to 30.0% weight percent of a particulate water-extractable organic or inorganic filler, such as sodium monosaccharide or disaccharide, sorbitol powder, mannitol, and the like.

The rate of release of remineralizing salt core matrix content of the encapsulated particles under aqueous conditions can be controlled by the quantity and type of polymer coating on the particle surface.

Low molecular weight hydrophilic polymers will release the particle core matrix content at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate. Polyvinylpyrrolidone will release the particle core matrix content at an immediate rate, when the encapsulated particles incorporated into a dentifrice, e.g., toothpaste or gel, are applied to the teeth.

A present invention encapsulated remineralizing salt particle composition exhibits a unique combination of properties because of the novel physical form of the free-flowing, but substantially inert, polymer-coated particles when utilized as an ingredient in a dentifrice.

Examples of suitable oleophilic coatings or enscapsulating materials include paraffin, mineral oil, edible oils such as peanut oil, coconut oil, palm oil, or safflower oil, oleophilic organic esters such as isopropyl siloxane myristate or isopropyl palmitate, edible polysiloxanes, and the like.

Encapsulating salts with a mixture of paraffin and waxes is also suitable.

By employing mineral oil as an oleophilic coating material for the calcium, phosphate and/or fluoride salts in the compositions of the invention, one other advantageous characteristic is provided. Specifically, oral bacteria known to be adversely affected by oleophilic materials. Thus, the mineral oil used in the compositions of the invention will help in removing undesired bacteria during the course of treatment.

The coating should be of a thickness and composition so that it either readily dissolves, disperses or emulsifies in water, e.g., in the mouth during brushing, or disintegrates during such action to release the active materials, i.e., one or more salts.

If the oleophilic material used for the coating is water insoluble, such as mineral oil, the coating phase can be pre-emulsified with a non-ionic, non-aqueous surfactant such as a hydrophilic ethoxylated sorbitan monooleate, e.g., the material sold under the trademark Tween. In this manner, when the composition is placed in water, the mineral oil or other olephilic coating on the particles is emulsified more readily than without the emulsification agent being present. Other similar surfactants can be employed such as sodium lauryl sulfate and other non-ionic surfactants.

In an embodiment of this invention there is provided a stable single-part non-aqueous dentifrice product for remineralizing dental enamel comprising: (i) from about 0.05% to 15.0%, preferably about 0.10% to 10.0%, water-soluble calcium salt; (ii) from about 0.05% to 15.0%, preferably about 0.10% to 10.0% water-soluble phosphate salt, optionally together with from about 0.01% to 10.0% and preferably from about 0.02% to 5.0% water-soluble fluoride salt, (iii) wherein there is an encapsulating coating on at least one of the water-soluble salts that either readily dissolves, disposes or emulsifies in water, e.g., saliva, and (iv) where in when the salts are contacted with water and/or saliva the pH is between about 4.5 and 10.0 and preferably between about 5.0 and 7.0.

In another embodiment of this invention there is provided a stable, single-part non-aqueous product for remineralization which can be reconstituted into a mouthwash by addition of water or into other products from the concentrate-like product. Accordingly the product comprises from about 1.0% to 80.0% of a calcium salt, from about 1.0% to 80.0% of a phosphate salt, from about 0.1% to 20.0% of a stabilizer comprising a material selected from at least one member of the group consisting of a dessicating agent and a coating of at least one of the water-soluble salts that either readily dissolves, disperses or emulsifies in water, from about 0.01% to 20.0% of a flavor, from about 0.01% to 30.% of a sweetener, from 0 to about 10.0% of a fluoride salt, from 0 to about 5.0% of a surfactant and wherein when the concentrate is mixed with water the pH of the resulting mixture is between about 4.5 and 10.0.

In still another embodiment of this invention there is provided a stable single-part non-aqueous product for remineralizing dental enamel comprising: (i) from about 0.05% to 15.0%, preferably about 0.10% to water-soluble calcium salt; (ii) from about 0.05% to 15.0%, preferably about 0.10% to water-soluble phosphate salt, optionally together with from about 0.01% to 10.0% and preferably from about 0.02% to 5.0% fluoride releasing agent, (iii) from about 0 to 7.5% of an orally acceptable dessicating agent; (iv) a hydrophilic, non-aqueous vehicle which is water-soluble; and (v) wherein when the salts are contacted with water or saliva the pH is between about 4.5 and 10.0 and preferably between about 5.0 and 7.0.

A plurality of packaging methods may be employed in order to contain or store the components and provide effective dispensing thereof into the oral cavity.

Thus, the components of a toothpaste, gel, cream, or the like, may be simultaneously dispensed from separate collapsible tubes preferably made of plastic, a plastic and metal laminate, etc.

The tubes of the above embodiments are usually filled from the bottom and are subsequently sealed together by conventional techniques.

Another alternative packaging arrangement comprises of a pressurized container which is provided with a compartment and a spout. The internal pressure of the compartment is maintained by a pressurized gas, i.e., nitrogen, at the bottom of the compartment. Operation of a mechanical actuator actuates a valve which releases the contents of the compartment through the spout causing discharge of the paste or gel components onto a brush.

The mouthwash or rinse and similar liquid embodiments are maintained in a manner similar to the pastes or gels in that during storage, each of the components are stabilized with regards to one another to prevent premature reaction. Upon dispensing, the components mix and react in the oral cavity to effect remineralization of dental enamel. The liquid components can therefore be stored in the compartment of a dispenser. The dispenser usually includes a closure system comprising for example, an inclined crown portion, a pouring spout extending upwardly from an upper surface of the crown portion and a cover for securement to the crown portion. The cover is provided with closure means, for example, depending plugs, to close the closure. The pouring spout is preferably provided with a vent opening in addition to a product orifice in the spouts. Transparent containers have proven to be the most satisfactory. Transparency aids a person's ability to accurately and controllably dispense relatively exact volumes from a dispenser. Transparent walled containers also serve as a window function for gauging the amounts of liquid remaining in the dispenser. The walls of the containers can be scribed or otherwise calibrated to assist in dispensing the correct remineralizing amount of product.

While applicants do not wish the scope of the present invention to be limited by theory, it is believed that the calcium, phosphate, and fluoride ions diffuse through the tooth surface to the demineralized subsurface and precipitate in the demineralized subsurface where they remineralize the tooth structure. This is surprising because sufficient calcium, phosphate, and fluoride ions remain soluble for a period of time sufficient to permit their diffusion into the demineralized subsurface of the dental enamel. This is accomplished by allowing the product to mix with saliva when applied to the teeth or by combining the particular ions just prior to their application to the teeth in a solution having a pH of about 4.5 to 10 and preferably from about 5.0 to 7 at which pH enough of the calcium, phosphate, and fluoride ions remain soluble for the period of time required to remineralize the lesions of the dental enamel. As hereinbefore described, salts yielding the calcium ions, phosphate ions, and if desired, fluoride ions are stored in a hydrophilic, non-aqueous vehicle and/or are stabilized against reaction to avoid the premature precipitation of calcium phosphate.

Chemically equivalent concentrations are not necessary as long as the molar ratio of calcium and phosphate ions in the mixture is from about 0.01 to up to 100 to 1. It is preferred that the ratio is from about 0.2 to 1 up to 5 to 1, and it is most preferred that the ratio is between about 1 to 1 and 1.67 to 1; the ratio of calcium to phosphate in insoluble calcium phosphate salts.

With regard to the length of time of exposure to the teeth of the solutions applied to, or formed in, the oral cavity it is necessary that the period of time be great enough to allow diffusion of the ions into the demineralized subsurface. At least about ten seconds are required for this diffusion. The paste, gel, or aqueous solution is preferably applied to the teeth for from about 10 seconds to about 5 minutes. The pH of the solution remains relatively constant after its introduction into the oral cavity. Calcium phosphate may precipitate at this pH, but most surprisingly while some of the precipitation may occur immediately and some small amount even before application to the teeth, sufficient calcium, phosphate and fluoride ions remain in solution to diffuse into the teeth and remineralize the demineralized dental enamel. It is believed that the ability of the solutions to provide ions for remineralization is greatest upon their first introduction into the oral cavity, thereafter decreasing.

With a toothpaste, gel, and the like, mixing is achieved on the surface to the teeth while brushing and with a liquid non-aqueous mouthwash upon introduction into the oral cavity. The essence of the present invention lies with the stable, single part product; in the mixing of the product components in the mouth; and the quick and timely application of the resulting aqueous solution which will precipitate calcium phosphate, calcium fluoride and calcium fluoroapatite in the subsurface enamel of the teeth. Before such precipitation occurs, the mixture comprising the aqueous solution must quickly be applied to the teeth. Surprisingly, the solution can have a pH of about 4.5 to 10, but preferably about 5.0 to 7 to achieve this result. At a pH below about 3, demineralization occurs rapidly. A pH below 2.5 is generally undesirable from a safety standpoint.

The pH of the solutions of the present invention may be adjusted to the pH desired by methods well known in the art. The pH may be controlled by the addition of any acid which is safe for use in the oral cavity and which yields the desired pH at the amount employed. Examples of suitable acids are acetic acid, phosphoric acid, hydrochloric acid, citric acid and malic acid; by the addition of a base, for example, sodium hydroxide; or buffered, for example with sodium citrate benzoate, carbonate, or bicarbonate, disodium hydrogen phosphate, sodium dihydrogen phosphate, etc. Preferably the remineralizing salts employed can be selected to obtain the desired pH. Usually a combination of monobasic, dibasic and/or tribasic alkali metal phosphate salt is selected to provide the target pH.

The following Examples illustrate the invention: In the Examples and elsewhere herein parts and percent are by weight unless otherwise stated.

EXAMPLE 1

In this example a non-aqueous product for testing was prepared and mixed with water Just previous to testing. The testing procedure was as follows:

Artificial lesions, about 50 u deep, were formed in one surface of bovine enamel chips using a demineralizing Carbopol gel, which was used to treat the specimens for 72 hours. The surface hardness of the surface to be treated was then measured.

The regimen cycle consisted of a 30 minute demineralization in a standard demineralizing solution followed by a 5 minute treatment of the test products diluted 1 part product to two parts human saliva, followed by a 60 minute remineralization in human saliva. Overnight, which was every fifth cycle, the specimens were kept with a layer of saliva and stored in a cold room. The test ran for three days, from a total of 15 demineralization:treatment:remineralization cycles.

For the treatment cycle, the remineralizing test agent of the example was diluted 1 part product to 2 parts saliva and mixed together immediately before immersion of the enamel specimens.

The non-aqueous oral remineralizing test agent was prepared as follows:

| | |
|---|---|
| Calcium nitrate | 4 |
| Dipotassium phosphate | 8.00 |
| Sodium fluoride | 0.55 |
| Glycerin | 50 |
| Acetic acid | To adjust pH of A & B mixture of 5.5 immediately after mixing. |

The above product was then mixed with 137.45 parts of water to solubilize the salts and then was diluted with saliva as described above.

HARDNESS INCREASE DUE TO TREATMENT
(Vickers Hardness Units)

| | Example 1 | Crest | 1200 ppm Fluoride at pH 5.5 | Placebo |
|---|---|---|---|---|
| 5 cycles | 17.0 + 1.9 | 11.8 + 1.4 | | |
| 10 cycles | 23.6 + 1.4 | 13.0 + 3.6 | 13.7 + 2.3 | 3.9 + 0.7 |
| 15 cycles | 34.8 + 2.8 | 11.2 + 1.7 | | |
| 20 cycles | 48.2 + 2.8 | 17.5 + 2.2 | | |

FLUORIDE INCREASE DUE TO TREATMENT (ug/cm$^3$)

| | | | | |
|---|---|---|---|---|
| 5 cycles | 2433 | 1879 | | |
| 10 cycles | 3523 | 2082 | 2928 | 244 |
| 15 cycles | 4431 | 2196 | | |
| 20 cycles | 4749 | 2964 | | |

The results show much greater remineralization, as measured by hardness increase and fluoride uptake, due to treatment with the product of Example 1 than Crest, fluoride solution or placebo.

EXAMPLES 2, 3, 4 and 5

Examples 2–5 illustrate various embodiments of remineralizing toothpaste formulation of the invention as follows:

| | Example | | | |
|---|---|---|---|---|
| | 2 | 3 | 4 | 5 |
| Glycerin | 65.56 | 0.00 | 0.00 | 59.54 |
| Carbowax 400 | 0.00 | 38.15 | 0.00 | 0.00 |
| Propylene glycol | 0.00 | 0.00 | 42.80 | 0.00 |
| Silica abrasive | 15.00 | 0.00 | 0.00 | 12.00 |
| Silica thickener | 8.00 | 4.00 | 4.00 | 6.00 |
| DCPDH* | 0.00 | 40.00 | 0.00 | 0.00 |
| Calcium chloride | 5.00 | 0.00 | 0.00 | 5.00 |
| Calcium glycerophosphate | 0.00 | 7.50 | 3.50 | 5.00 |
| Disodium phosphate | 3.70 | 7.50 | 6.50 | 10.00 |
| Sodium meta-phosphate | 0.00 | 0.00 | 38.00 | 0.00 |
| Sodium lauryl sulfate | 1.50 | 1.70 | 1.20 | 1.00 |
| Sodium fluoride | 0.24 | 0.00 | 0.00 | 0.00 |
| Stannous fluoride | 0.00 | 0.00 | 1.80 | 0.00 |
| Sodium MFP | 0.00 | 0.00 | 0.00 | 0.76 |
| Flavor | 0.80 | 0.90 | 0.90 | 0.70 |
| Saccharin | 0.20 | 0.20 | 0.30 | 0.20 |

*DCPDH = Dicalcium phosphate dihydrate

Example 6 illustrates an embodiment of a remineralizing mouthwash formulation and Example 7 illustrates a dry-mix concentrate suitable for dilution as follows:

| | Example 6 | Example 7 |
|---|---|---|
| Glycerin | QS | |
| Ethanol | 5.00 | |
| Sodium MFP | 0.20 | |
| Calcium nitrate | 7.00 | 50 |
| Monopotassium phosphate | 4.00 | 41.725 |
| Sodium fluoride | | 0.275 |
| Spray dried flavor | 1.0 | 5.0 |
| Aspartame | 0.6 | 3.0 |

Example 7 is diluted 5 g to 100 g water before use.

EXAMPLES 8–11

Example 8–11 illustrate dry-mix concentrated formulations which can be diluted with water when they are to be employed.

| | Example | | | |
|---|---|---|---|---|
| | 8 | 9 | 10 | 11 |
| Calcium lactate pentahydrate | 59.7 | | | |
| Calcium acetate anhydrous | | 40.0 | | |
| Calcium gluconate | | | 65.0 | |
| Encapsulated* calcium nitrate 97% | | | | 45.4 |
| Magnesium chloride | | | 10.0 | |
| Monopotassium phosphate | 30.0 | 28.0 | | 21.0 |
| Dipotassium phosphate | | 8.0 | | |
| Monosodium phosphate | | | 12.5 | |
| Disodium phosphate | | | 2.5 | 7.0 |
| Sodium fluoride | 0.3 | | | |
| Stannous fluoride | | | 2.5 | |
| Sodium MFP | | | | 3.6 |
| Flavor | 6.0 | 4.0 | 5.0 | 15.0 |
| Saccharin | 3.0 | | 2.5 | 8.0 |
| Aspartame | | 20.0 | | |

*Caclium nitrate encapsulated with water soluble ethyl cellulose encapsulent
Usage Concentration 1.0 g per oz, 0.75 g per oz, 1.2 g per oz, 0.42 g per oz Examples 12–14 each illustrate a formulation which can be employed as an efferevercent mouthwash when dilutent with water.

|  | Example | | |
|---|---|---|---|
|  | 12 | 13 | 14 |
| Calcium acetate anhydrous |  | 30.0 |  |
| Encapsulated* calcium nitrate 97% | 26.0 |  | 36.0 |
| Monopotassium phosphate | 20.0 | 28.0 | 30.0 |
| Malic acid | 16.0 | 17.0 | 11.0 |
| Magnesium chloride |  |  | 5.0 |
| Sodium bicarbonate | 10.0 | 15.0 | 10.0 |
| Sodium fluoride | 2.0 |  | 2.0 |
| Flavor | 6.0 | 5.5 | 4.0 |
| Saccharin |  | 4.5 | 2.0 |
| Aspartame | 20.0 |  |  |

*Calcium nitrate encapsulated with water soluble ethyl cellulose encapsulent
Usage Concentration    5.0 g per oz    4.0 g per oz    5.0 g per oz

What is claimed is:

1. A stable, single part, non-aqueous product for remineralizing lesions in teeth comprising:
   (i) from about 0.05% to 15.0% of at least one water-soluble calcium salt;
   (ii) from about 0.05% to 15.0% of at least one water-soluble phosphate salt; and
   (iii) a stabilizer comprising a material selected from at least one member of the group consisting of up to about 7.5% of a dessicating agent and a coating on at least one of the water-soluble salts that either readily dissolves, disperses or emulsifies in water;
   (iv) wherein when the components are mixed with water or saliva the pH of the mixture is between about 4.5 and 10.0.

2. The product according to claim 1 wherein the product contains from about 0.01% to 5.0% of at least one water-soluble fluoride salt which yields fluoride ions.

3. The product according to claim 1 wherein the product contains from about 0.10% to 10.0% of said calcium salt.

4. The product according to claim 1 wherein the product contains from about 0.10% to 10.0% of said phosphate salts.

5. The product according to claim 4 wherein the product contains from about 0.02% to 2.0% of said fluoride salt.

6. The product according to claim 1 wherein the pH of the mixture is from about 5.0 to 7.0 upon mixing.

7. The product according to claim 1 wherein the molar ratio of calcium and phosphate ions in the two components is from about 0.01 to 1 up to 100.0 to 1.

8. The product according to claim 7 wherein the molar ratio of calcium and phosphate ions in the two components is from about 0.2 to 1 up to 5.0 to 1.

9. The product according to claim 1 wherein said product is in the form of a powder granular material, flake, or tablet.

10. The product according to claim 1 wherein the said product contains from about 100 ppm to 35,000 ppm calcium ions and from about 100 ppm to 40,000 ppm phosphate ions.

11. The product according to claim 1 wherein said product contains from about 20 ppm to 5,000 ppm fluoride ions.

12. A method for remineralizing lesions in teeth comprising:
   (i) applying to the teeth a stable, single part, non-aqueous composition comprising from about 0.05% to 15.0% of at least one water-soluble calcium salt; from about 0.05% to 15.0% of at least one water-soluble phosphate salt; and a stabilizer comprising of a material selected from at least one member of the group consisting of up to about 7.5% of a dessicating agent and a coating on at least one of the water-soluble salts that either readily dissolves, disperses or emulsifies in water
   (ii) contacting the composition with an aqueous solvent for the salts comprised of water or saliva wherein the resulting mixture has a pH of from about 4.5 to 10.0; and
   (iii) applying said mixture as an aqueous solution to the teeth for a sufficient time that the calcium and phosphate ions from each of the salts diffuse into the subsurface of demineralized enamel and subsequently precipitate to form hydroxyapatite and remineralize the dental enamel.

13. The method according to claim 12 wherein the product is in the form of a powder, granular material, flake, or tablet.

14. The method according to claim 12 wherein the product contains a hydrophilic, non-aqueous vehicle which is water-soluble.

15. The method according to claim 14 wherein the product applied to the teeth is a non-aqueous paste, a gel, or a professional gel and is extruded onto a toothbrush.

16. The method according to claim 12 wherein the product applied to the teeth is a non-aqueous mouthwash or rinse.

17. The method according to claim 12 wherein the period of application of calcium and phosphate ions to the teeth is from about 10 seconds up to 15 minutes.

18. The method according to claim 12 wherein the product contains from about 0.10% to 10.0% of said calcium salt.

19. The method according to claim 12 wherein the product contains from about 0.10% to 10.0% of said phosphate salt.

20. The product according to claim 12 wherein the product contains from about 0.01% to 4.0% of at least one water-soluble fluoride salt which yields fluoride ions.

21. The product according to claim 20 wherein the product contains from about 0.02% to 2.0% of said water-soluble fluoride salt.

22. The method according to claim 12 wherein the resulting dissolved product has a pH of from about 5.0 to 7.0.

23. The method according to claim 12 wherein the molar ratio of calcium and phosphate ions is from about 0.01 to 1 up to 100.0 to 1.

24. The method according to claim 23 wherein the molar ratio of calcium and phosphate ions is from about 0.2 to 1 up to 5.0 to 1.

25. The method according to claim 13 wherein the product contains from about 100 ppm to 35,000 ppm calcium ions and from about 100 ppm to 40,000 ppm phosphate ions.

26. The method according to claim 13 wherein the product contain from about 20 ppm to 5,000 ppm fluoride ions.

* * * * *